(12) United States Patent
Okamura et al.

(10) Patent No.: US 10,456,503 B2
(45) Date of Patent: Oct. 29, 2019

(54) POLYMER LAMINATE

(71) Applicants: Tokai University Educational System, Tokyo (JP); Toray Industries, Inc., Tokyo (JP)

(72) Inventors: Yosuke Okamura, Hiratsuka (JP); Yu Nagase, Hiratsuka (JP); Takuya Komachi, Hiratsuka (JP); Motonori Hochi, Otsu (JP); Yuki Sekido, Otsu (JP); Toru Arakane, Tokyo (JP)

(73) Assignees: Toray University Educational System, Tokyo (JP); Toray Industries, Inc., Tokyo (JP)

( * ) Notice: Subject to any disclaimer, the term of this patent is extended or adjusted under 35 U.S.C. 154(b) by 192 days.

(21) Appl. No.: 15/305,460

(22) PCT Filed: Apr. 20, 2015

(86) PCT No.: PCT/JP2015/062008
§ 371 (c)(1),
(2) Date: Oct. 20, 2016

(87) PCT Pub. No.: WO2015/163289
PCT Pub. Date: Oct. 29, 2015

(65) Prior Publication Data
US 2017/0043062 A1 Feb. 16, 2017

(30) Foreign Application Priority Data

Apr. 24, 2014 (JP) ................. 2014-089973

(51) Int. Cl.
| | |
|---|---|
| *B32B 27/02* | (2006.01) |
| *A61L 31/00* | (2006.01) |
| *A61L 15/16* | (2006.01) |
| *B32B 27/36* | (2006.01) |
| *B32B 27/08* | (2006.01) |
| *B32B 27/30* | (2006.01) |
| *A61L 31/04* | (2006.01) |
| *A61L 31/06* | (2006.01) |
| *A61L 31/14* | (2006.01) |
| *A61L 15/24* | (2006.01) |
| *A61L 15/26* | (2006.01) |
| *A61L 15/28* | (2006.01) |
| *A61L 15/64* | (2006.01) |
| *B32B 9/02* | (2006.01) |
| *B32B 9/04* | (2006.01) |
| *B32B 7/05* | (2019.01) |

(52) U.S. Cl.
CPC ............. *A61L 31/00* (2013.01); *A61L 15/16* (2013.01); *A61L 15/24* (2013.01); *A61L 15/26* (2013.01); *A61L 15/28* (2013.01); *A61L 15/64* (2013.01); *A61L 31/042* (2013.01); *A61L 31/048* (2013.01); *A61L 31/06* (2013.01); *A61L 31/148* (2013.01); *B32B 7/05* (2019.01); *B32B 9/02* (2013.01); *B32B 9/04* (2013.01); *B32B 9/045* (2013.01); *B32B 27/08* (2013.01); *B32B 27/306* (2013.01); *B32B 27/36* (2013.01); *A61L 2400/12* (2013.01); *B32B 2250/05* (2013.01); *B32B 2250/24* (2013.01); *B32B 2250/44* (2013.01); *B32B 2307/7163* (2013.01); *B32B 2307/73* (2013.01); *B32B 2535/00* (2013.01)

(58) Field of Classification Search
CPC ........ B32B 2307/7163; B32B 2307/73; B32B 2535/00; B32B 27/08; B32B 27/30; B32B 27/306; B32B 27/36
See application file for complete search history.

(56) References Cited

U.S. PATENT DOCUMENTS

| | | | |
|---|---|---|---|
| 5,310,587 A * | 5/1994 | Akahori | B32B 7/02 428/35.2 |
| 2003/0180251 A1 | 9/2003 | Friedrich et al. | |
| 2007/0027550 A1 | 2/2007 | Farnsworth et al. | |
| 2007/0298237 A1* | 12/2007 | Goino | C08K 5/0075 428/304.4 |
| 2010/0062258 A1 | 3/2010 | Takeoka et al. | |
| 2010/0063580 A1* | 3/2010 | McClain | A61L 31/10 623/1.15 |
| 2016/0002422 A1 | 1/2016 | Hochi et al. | |
| 2016/0121031 A1 | 5/2016 | Morinaga et al. | |

FOREIGN PATENT DOCUMENTS

| | | | |
|---|---|---|---|
| JP | 2001-192337 A | | 7/2001 |
| JP | 2003-153999 A | | 5/2003 |
| JP | 2004-504887 A | | 2/2004 |
| JP | 2004-65780 A | | 3/2004 |
| JP | 2009-502329 A | | 1/2009 |

(Continued)

OTHER PUBLICATIONS

Written Opinion dated Jun. 23, 2015, of corresponding PCT Application No. PCT/JP2015/062008.
Fujie, T., et al., "Construction of Polymer Ultra-Thin Films (Nanosheets) as Medical Materials," *Convertech*, Converting Technical Institute, 2008, vol. 36, No. 10, pp. 137-143, along with an English translation of relevant portions.

(Continued)

*Primary Examiner* — Lawrence D Ferguson
(74) *Attorney, Agent, or Firm* — DLA Piper LLP (US)

(57) ABSTRACT

A polymer laminate has 2-100 layers each containing a biodegradable resin and having a thickness of 10 nm-400 nm that are laminated, the thickness of at least one of the outermost layers is 10 nm-180 nm, and the outermost layers are joined to each other. A polymer laminate excellent in biocompatibility and mechanical strength and suitable to medical applications such as wound dressings and antiadhesive materials can be obtained.

15 Claims, 5 Drawing Sheets

(56) References Cited

FOREIGN PATENT DOCUMENTS

| JP | 2010-131163 A | 6/2010 |
|----|---------------|--------|
| JP | 2010-187950 A | 9/2010 |
| JP | 2012-187926 A | 10/2012 |
| WO | 2005/094915 A1 | 10/2005 |
| WO | 2014/141983 A1 | 9/2014 |

OTHER PUBLICATIONS

Takeoka, S., et al., Possibility of Polymer-based Nanosheet as Wound Dressings and Anti-adhesion Materials in Surgery, *Material Stage*, Technical Information Institute Co., Ltd., 2012, vol. 12, No. 7, pp. 16-19, along with an English translation of relevant portions.
Shimono, H., et al., "Construction of Polylactic Nanosheet and Effect for Wound Dressings using Mouse Stomach Incision Model," *Polymer Preprints*, The Society of Polymer Science, Japan, vol. 58, No. 1, 2009, p. 1884, along with an English translation of the relevant portions.
Komachi, T., et al., "Fabrication of Multi-layered Nanosheet and Biomedical Applications as Wound Dressings," *Polymer Preprints*, The Society of Polymer Science, Japan, vol. 63, No. 1, May 2009, pp. 2983-2984, along with an English translation of relevant portions.
Okamura, Y., "Preparation of Layered Polymer Ultra-thin film and Application to Wound Dressing Material for Lever," *Preprints*, Japanese Society for Biomaterials, 36th Annual Meeting of Japanese Society for Biomaterials. Nov. 2014, p. 98, along with an English translation of relevant portions.

* cited by examiner

21 Bovine serum albmin (rhodamine label attached)

22 PLLA resin layer (5 layers, DiOC18 labelling)

200nm Latex beads

FIG. 13

1000 nm Latex beads

POLYMER LAMINATE

TECHNICAL FIELD

This disclosure relates to a polymer laminate having a layered structure the respective layers of which have a thickness of 10 nm to 400 nm, and suitable to use for medical applications such as wound dressings and antiadhesive materials.

BACKGROUND

In a surgical operation represented by abdominal surgery, plastic surgery, neurosurgery or the like, there is a problem of adhesion between organs as one of complications after operation. This is caused from the phenomenon wherein, when normal tissues having received injury due to drying and oxidation are stitched to each other to be closed in the operation, in a process of being self-healed by healing of wound, an adhesion phenomenon, namely, conjugation of the tissues of organs to each other which essentially must not happen, may be caused. It is said that adhesion is caused at a high possibility in a surgical operation, the adhesion may lead to pain or complications causing a serious symptom such as ileus or sterility.

It is difficult to treat an adhesion once caused, with medicine. Further, ileus due to an adhesion may be caused even after several years have passed after an operation. It is believed that adhesion can be treated only by adhesion separation surgery which separates the adhesion part by conducting surgical operation again and, therefore, in a surgical operation, prevention of adhesions is extremely important.

So far, as the treatment to prevent tissue adhesion or delay of healing after operation, a method of covering an exposed organ tissue with a piece of gauze dipped in a saline to prevent drying and oxidation has been employed. However, because an organ has a complicated and flexible property, the method has been origins causing problems such as ones that a sufficient covering cannot be carried out by gauze, that gauze becomes an obstacle relative to performing the operation by the doctor, and that the possibility of leaving gauze in the body is increased because much gauze is used.

From such reasons, as the materials having an effect of preventing adhesion or preventing delay of healing, a method of using a silicone, "TEFLON" (registered trademark), a polyurethane, an oxycellulose and the like as an adhesion preventive membrane has been employed to physically separate origin tissues. However, because these materials are non-absorbent materials, they are left on the surface of the biological tissue, and not only do they delay repair of the tissue but also they become originators of infection and inflammation.

In recent years, to solve such problems, antiadhesive materials using gelatin or collagen that can expect bioabsorbability are reported (JP 2004-065780 A and JP 2001-192337 A). Further, an antiadhesive material using a polysaccharide such as trehalose which has no risk of infectious disease (JP 2003-153999 A) and an antiadhesive material using a hyaluronic acid (WO 2005/094915) are also reported.

However, in antiadhesive materials using gelatin or collagen as described in JP 2004-065780 A and JP 2001-192337 A, there is a problem where it is difficult to remove telopeptide part having an antigenicity and, further, because there is a risk of an animal-derived infectious disease such as prion contamination, it is better to avoid use to an organism. Moreover, there are many instances where a crosslinking agent added to obtain strength and control degradability is not preferred for use in an organism. Furthermore, in a natural polymer such as gelatin or collagen, there is such a problem that it is low in strength though it is high in affinity with skin. Therefore, in a natural polymer, although it is necessary to ensure a strength by a material crosslinked with a crosslinking agent or by use of a reinforcement material or by wrapping with a gauze, when a reinforcement material is used, because there are many instances where the structure becomes complicated, it is not practical.

Further, in an antiadhesive material using a polysaccharide as described in JP 2003-153999 A, the strength of a polysaccharide is poor, and there is a problem that suture is difficult because of lack of strength. Further, even if suture is possible, it is difficult to maintain a sutured state for a certain period of time.

Further, in an antiadhesive material using a hyaluronic acid as described in WO 2005/094915, because of its poor close adherence with an organ, the antiadhesive material and the organ are liable to be shifted from each other, and whereby an adhesion may be caused and, therefore, it is not always said that it has a satisfactory performance and, further, there is a problem that it is high in manufacturing cost because it is difficult to serve it to mass production. To solve these problems, although there are a method of using blood products and a method of using chemical substances to strongly bring the antiadhesive material into close contact with the organ and the like, these methods include a problem that high-quality management in viewpoints of hygiene and safety is required and it is difficult to be handled.

Furthermore, in the antiadhesive materials disclosed in JP 2004-065780 A, JP 2001-192337 A, JP 2003-153999 A and WO 2005/094915 (gelatin, collagen, polysaccharide, natural polymer, hyaluronic acid and the like), it is difficult to be adapted to use requiring a high mechanical strength (an affected part high in pressure load ascribed to a body fluid such as blood or an expiration).

Thus, although there are many reports relating to materials to prevent tissue adhesion, a material having a satisfactory performance (close adherence with an organ, mechanical strength) as an antiadhesive material has not been obtained. Namely, a material capable of preventing adhesion until a tissue is recovered and maintaining a strength until the tissue is recovered, without causing the above-described problems, is required.

Accordingly, in consideration of the background of such conventional technologies, it could be helpful to provide a polymer laminate excellent in biocompatibility and mechanical strength and also capable of containing chemicals and particles.

SUMMARY

We thus provide:

(1) A polymer laminate in which 2-100 layers each containing a biodegradable resin and having a thickness of 10 nm to 400 nm are laminated, a thickness of at least one of outermost layers is 10 nm to 180 nm, and the outermost layers are joined to each other.

(2) The polymer laminate according to (1), wherein the above-described at least one of outermost layers contains a polylactic acid-based resin.

(3) The polymer laminate according to (1) or (2), wherein at least one layer of the layers having a thickness of 10 nm to 400 nm contains a compound selected from the group consisting of a polysaccharide, a polyvinyl alcohol and a polyvinyl alcohol copolymer.

(4) The polymer laminate according to (3), wherein the polysaccharide is an alginate.

(5) The polymer laminate according to any one of (1) to (4), wherein a total thickness of the polymer laminate is 20 nm-1,000 nm. The definition of the total thickness of the polymer laminate will be described later.

(6) The polymer laminate according to any one of (1) to (5), wherein a hydrophobic chemical is contained in at least one layer of the layers having a thickness of 10 nm to 400 nm.

(7) The polymer laminate according to any one of (1) to (6), wherein a water soluble chemical is contained in at least one layer of the layers having a thickness of 10 nm to 400 nm.

(8) The polymer laminate according to any one of (1) to (7), wherein particles having a particle diameter of 5 nm to 5,000 nm are contained in at least one interlaminar part formed between the layers having a thickness of 10 nm to 400 nm.

In the polymer laminate, since it is a laminate wherein 2-100 layers each containing a biodegradable resin and having a thickness of 10 nm to 400 nm are laminated, it has both of a high flexibility and a high mechanical strength (in particular, resistance against a pressure receiving at a local part of surface).

Further, since the thickness of at least one of outermost layers is 10 nm to 180 nm, it can have high followability, coatability and close adherence relative to a surface shape of an adherend (in particular, one having a flexibility such as an organ).

In addition, since the outermost layers are joined to each other, the respective layers can have a high shape retention property as a laminate without being scattered against a mechanical stress received from outside.

Further, by containing a polylactic acid-based resin in at least one of the outermost layers, a high temporal stability (with shape) as a laminate can be given, and the handling ability can be improved.

Furthermore, by containing at least one compound selected from the group consisting of a polysaccharide, a polyvinyl alcohol and a polyvinyl alcohol copolymer in at least one layer of the layers containing a biodegradable resin, it becomes possible to laminate multi layers each containing a biodegradable resin and, in particular, by utilizing the gelation and dissolution operation of an alginate among the polysaccharides, it is facilitated to join the outermost layers to each other.

From such effects obtained, the polymer laminate is optimum as external skin preparations such as wound dressings, antiadhesive materials and skin-care products.

In addition, the polymer laminate can be used also as a drug delivery system by providing a layer containing a chemical at an interlaminar part or by containing a chemical in a layer itself. In particular, because it is formed as a lamination structure, for each layer or each interlaminar part, the timing for loading or sustained release of various different kinds of chemicals can be controlled. In particular, a local chemical dosage is facilitated by sticking it on an affected part at a plane form like a film or a sheet. For example, a hydrophobic chemical can be contained in at least one layer of the above-described layers having a thickness of 10 nm-400 nm. Further, a water soluble chemical can also be contained in at least one layer of the above-described layers having a thickness of 10 nm-400 nm.

Furthermore, except chemicals, particles may be contained in a layer itself or in an interlaminar part.

Further, by controlling the total thickness of 20 nm to 1,000 nm, optimum handling ability, shape followability and mechanical strength can be given together.

Furthermore, when at least one of the outermost layers contains a polylactic acid-based resin, because the sticking surface of the polylactic acid-based resin, which is the outermost layer, is transparent, a scar is not conspicuous and, therefore, it can be applied not only to surgery operation but also to sticking to a skin, and also to use as a plaster.

EXPLANATION OF SYMBOLS

1: layer containing biodegradable resin
2: joining portion of outermost layers to each other
11: sample for determination
12: washer
13: bulge testing machine
14: syringe pump
15: gauge pressure gauge
21: bovine serum albumin
22: PLLA resin layer

DETAILED DESCRIPTION

Hereinafter, our laminates and methods will be explained in detail together with examples thereof.

Thickness of Layer and Number of Layers of Polymer Laminate

The thickness of each layer of a polymer laminate is 10 nm to 400 nm from the viewpoint of flexibility and mechanical strength, and it is preferably 20 nm to 180 nm, and more preferably 20 nm to 100 nm. If less than 10 nm, it may become difficult to keep the shape of each layer itself, and if more than 400 nm, it may become difficult to have flexibility and close adherence together.

The number of layers of a polymer laminate is 2 to 100 layers from the viewpoint of flexibility and mechanical strength, and it is preferably 3 to 21 layers, and more preferably 5 to 21 layers. The outermost layers are included in the number of layers. In a single layer, it may become difficult to have mechanical strength and flexibility together, and even when laminated, if more than 100 layers, economic efficiency and productivity may be damaged.

The thickness of at least one of the outermost layers of a polymer laminate is 10 nm to 180 nm from the viewpoint of followability, coatability and close adherence relative to an adherend, and it is preferably 20 nm to 120 nm. If less than 10 nm, it may become difficult to keep the shape of each layer itself, and if more than 180 nm, it may become difficult to have flexibility and close adherence together.

Joining State of Outermost Layers to Each Other

In the polymer laminate, the outermost layers are joined to each other. The outermost layers mean layers forming two surfaces positioned at the outermost sites in the laminate. Further, the joining means a state where the two outermost layers are integrated at least partially, for example, a state where the outermost layers are, at least partially, fused, adhered, bonded, combined, fixed, adsorbed or stitched to each other. Although the structure for joining the outermost layers to each other in the polymer laminate is not particularly limited, for example, as shown in FIGS. 1 to 8, the outermost layers of laminated layers 1 each containing a biodegradable resin can be joined to each other by a joint portion 2. More concretely, a formation wherein the outermost layers and the layers other than the outermost layers are joined to each other as exemplified in FIGS. 1 and 2, a formation wherein the outermost layers are joined to each other at pinpoints as exemplified in FIGS. 3 and 4, a formation wherein the outermost layers are joined to each other at a part of the end portion of the laminate as exemplified in FIGS. 5 and 6, a formation wherein the outermost layers are joined to each other at the entire part of the end portion of the laminate as exemplified in FIGS. 7 and 8, can be employed, and two or more formations shown in FIGS. 1 to 8 may be combined. Further, the layers other than the outermost layers either may be joined or may not be joined to the outermost layer.

Although a method of joining the outermost layers to each other in the polymer laminate is not particularly limited, for example, it is possible to employ a heat seal to melt by a heat sealer and bonding the layers each containing a biodegradable resin to each other, a welding seal, a fusing seal, a ultrasonic seal, a high-frequency seal or the like and, for example, a heat sealer can be used. Further, with respect to the temperature at the time of heat seal, it is preferred to employ a temperature of 0° C. or higher and 35° C. or lower than the melting point of the biodegradable resin. If the temperature at the time of heat seal is over a temperature higher than the melting point of the biodegradable resin by 35° C., the laminate may be completely molten, scorching is caused, or the appearance is damaged by thermal deformation of a portion other than the sealed portion. Further, if the temperature is below a temperature lower than the melting point by 0° C., the heat seal may not be performed sufficiently and delamination may be caused at the adhesive part. The time, the pressure and the like at the time of heat seal can be selected at an arbitrary condition as long as the temperature is controlled within the above-described range. Further, the temperature, when the biodegradable resin comprises a plurality of components, is preferably set at a standard of a resin having a lowest melting point.

Further, for the purpose of controlling the close adherence state after heat seal, a discrete-point seal may be performed by forming a hot plate by mechanically or chemically providing grooves to a plate composed of a metal such as a steel, a stainless or a copper, installing a heater such as a nichrome wire in the hot plate and heating the hot plate at a temperature of 60 to 270° C., nipping a polymer laminate between two hot plates, and applying a constant pressure (for example, 0.2 to 10 kg/cm$^2$) for a constant time (for example, 0.1 to 3.0 seconds).

Total Thickness of Polymer Laminate

The total thickness of a polymer laminate is preferably 20 nm to 1,000 nm from the viewpoint of followability, coatability and close adherence relative to an adherend, more preferably 100 nm to 800 nm, and particularly preferably 120 nm to 700 nm. If less than 20 nm, the mechanical strength and the handling ability may be lowered, and if more than 1,000 nm, the followability, coatability and close adherence relative to an adherend having a complicated surface shape may be lowered. The total thickness of a polymer laminate means a thickness summing the respective thicknesses of all layers of the laminated layers each containing a biodegradable resin and having a thickness of 10-400 nm and the outermost layers, and it means a summed thickness calculated removing the portions used for the above-described joining and the particle portions when particles are contained in interlaminar parts. When the thickness is dispersed depending upon determined places, an average value is employed.

Biodegradable Resin

Although the biodegradable resin is not particularly restricted, exemplified are aliphatic polyesters represented by a polylactic acid (PLA)-based resin, a polyglycolic acid, a poly(3-hydroxybutyrate), a poly(3-hydroxybutyrate-3-hydroxyvalerate), a poly(3-hydroxybutyrate-3-hydroxyhexanoate), a polycaprolactone, a polyethylene succinate, a polybutylene succinate, a polybutylene succinate adipate or the like, aliphatic aromatic polyesters represented by a polyethylene succinate terephthalate, a polybutylene succinate terephthalate, a polybutylene adipate terephthalate or the like, a polyvinyl alcohol or a copolymer thereof, polysaccharides such as a dextran, an agarose, a pullulan, a chitosan, a mannan, a carrageenan, an alginate, a starch group (oxidized starch, etherified starch, dextrin or the like), an amylose, an amylopectin, a pectin, a lentinan, a hyaluronic acid, a hylan, a cellulose derivative (methyl cellulose, ethyl cellulose, carboxymethyl cellulose, carboxyethyl cellulose, hydoxyethyl cellulose, hydoxypropyl cellulose or the like) and the like, polypeptides such as a gelatin, a collagen, an elastin, an albumin, a hemoglobin, a transferrin, a globulin, a fibrin, a fibrinogen, a keratin sulphate or the like, a resin comprising a thermoplastic starch, or a starch and an aliphatic (aromatic) polyester and the like.

In particular, from the viewpoint of mechanical strength and temporal stability as a physical barrier material, a polylactic acid-based resin is preferred. On the other hand, from the viewpoint of chemical loading property, flexibility and solubility in water, a polyvinyl alcohol or polyvinyl alcohol copolymer and an alginate are preferred.

As described later, the mechanical strength of a polymer laminate can be evaluated by determining a rapture strength of the polymer laminate by a bulge tester shown in FIG. 9.

Polylactic Acid-Based Resin

It is preferred that the main component of the polylactic acid-based resin is poly-L-lactic acid (L body) and/or poly- D-lactic acid (D body). The main component means that the content of the components originating from lactic acid is 70 mol % to 100 mol % relative to 100 mol % of all monomer components forming the polylactic acid-based resin, and a homo-polylactic acid-based resin substantially composed of only poly-L-lactic acid and/or poly-D-lactic acid is preferably used.

The weight average molecular weight of the polylactic acid-based resin is preferably at least 50,000 or more, in particular 50,000 to 400,000, and more preferably 50,000 to 300,000. The weight average molecular weight means a molecular weight determined with a good solvent such as chloroform, dichloromethane, or hexafluoroisopropanol (HFIP) by gel permeation chromatography (GPC), and calculated by conversion method with polymethyl methacrylate (PMMA).

By controlling the weight average molecular weight of the polylactic acid-based resin to be 50,000 or more, the mechanical properties of the layer containing the polylactic acid-based resin can be controlled to be excellent and, further, the mechanical properties of the polymer laminate also can be controlled to be excellent.

The polylactic acid-based resin may be mixed with a homo-polylactic acid-based resin having a crystallinity and an amorphous homo-polylactic acid-based resin for the purpose of improving the solubility into a solvent at the time of preparing a coating liquid for a coating layer. In this case, the rate of the amorphous homo-polylactic acid-based resin may be decided within a range which does not damage the desired effects. Further, when making a polymer laminate comprising a water soluble resin layer and a polylactic acid-based resin layer, when a relatively high thermal resistance is desired to be provided, at least one of the polylactic acid-based resins used preferably includes a polylactic acid-based resin having an optical purity of 95% or more.

The polylactic acid-based resin may be a copolymerized polylactic acid-based resin copolymerized with another monomer component having an ester forming function other than L-lactic acid and D-lactic acid. As a monomer component capable of being copolymerized, can be exemplified a hydroxycarboxylic acid such as glycolic acid, 3-hydroxybutyric acid, 4-hydroxybutyric acid, 4-hydroxyvaleric acid, and 6-hydroxy-caproic acid, and in addition, compounds containing a plurality of hydroxyl groups in a molecule such as ethylene glycol, propylene glycol, butane diol, neopentyl glycol, polyethylene glycol, glycerin, or pentaerythritol, or derivatives thereof, and compounds containing a plurality of carboxylic groups in a molecule such as succinic acid, adipic acid, sebacic acid, fumaric acid, terephthalic acid, isophthalic acid, 2,6-naphthalene dicarboxylic acid, 5-sodium sulfoisophthalic acid, and 5-tetrabutylphosphonium sulfoisophthalic acid, or derivatives thereof. Among the above-described copolymerized components, it is preferred to select a component having a biodegradability depending upon uses. It is preferred that these copolymerized components are contained at 0 mol % to 30 mol % relative to 100 mol % of all monomer components forming the polylactic acid-based resin. "0 mol %" means that a structure containing no copolymerized components may be possible.

As the method of producing a polylactic acid-based resin, though the details will be described later, a direct copolymerization from a lactic acid, a ring-opening copolymerization via a lactide, or the like, can be raised.

From the viewpoint of suppressing reduction of strength due to hydrolysis thereby providing a good durability (a long-term preservation property), the concentration of carboxylic end groups in the polylactic acid-based resin is preferably 30 equivalents/$10^3$ kg or less, more preferably 20 equivalents/$10^3$ kg or less, and further preferably 10 equivalents/$10^3$ kg or less. When the concentration of carboxylic end groups in the polylactic acid-based resin is 30 equivalents/$10^3$ kg or less, because the concentration of carboxylic end groups which also cause autocatalysis for hydrolysis is sufficiently low, a practically good durability is provided, and such a condition is preferred. The lower limit of the concentration of carboxylic end groups in the polylactic acid-based resin is not particularly restricted, and there is no problem even if it is as close to 0 equivalent as possible.

As the method of controlling the concentration of carboxylic end groups in the polylactic acid-based resin at a condition of 30 equivalents/$10^3$ kg or less, for example, can be exemplified a method of controlling it by the catalyst or thermal history at the time of synthesis of the polylactic acid-based resin, a method of reducing the thermal history by lowering the processing temperature or shortening the heating time for forming it in a film shape, a method of closing the ends of the carboxylic groups using a reaction type compound or the like.

In the layers containing the polylactic acid-based resin, for the purpose of improving the mechanical strength, an impact resistance improving agent may be contained at 2 mass % to 20 mass % relative to 100 mass % of the whole of the polymer laminate. Preferably, it is 2.5 mass % to 15 mass %. As the content of the impact resistance improving agent increases, the improvement effect of the impact resistance increases but, frequently, a great improvement of mechanical properties cannot be achieved even if it is contained at a content over 20 mass %.

As the impact resistance improving agent used to improve the impact resistance, aliphatic polyesters or aliphatic aromatic polyesters other than the polylactic acid-based resin are preferred from the viewpoint that they have a good dispersibility in the polylactic acid-based resin and a higher effect can be obtained by a small amount thereof.

The aliphatic polyesters or aliphatic aromatic polyesters other than the polylactic acid-based resin are not particularly limited, and concretely, can be exemplified a polyglycolic acid, a poly(3-hydroxybutyric acid), a poly(4-hydroxybutyric acid), a poly(4-hydroxyvaleric acid), a poly(3-hydroxyhexanoic acid) or a polycaprolactone, a polyethylene adipate, a polyethylene succinate, a polybutylene succinate, a polybutylene succinate adipate and the like.

Furthermore, to improve the mechanical properties and maintain the biodegradability, a polybutylene succinate-based resin, which is an aliphatic polyester other than the polylactic acid-based resin, is preferably used. More preferably, a polybutylene succinate or a polybutylene succinate adipate, which is great in effect for improving mechanical properties and excellent in compatibility with the polylactic acid-based resin, is used.

The weight average molecular weight of the polybutylene succinate-based resin is preferably 100,000 to 300,000. The polybutylene succinate-based resin is obtained by polycondensation of 1,4-butane diol and succinic acid.

The polylactic acid-based resin can be prepared, for example, by the following method. As the raw material, a lactic acid component of L-lactic acid or D-lactic acid and the aforementioned hydroxycarboxylic acid other than the lactic acid component can be used together. Further, cyclic ester intermediates of the hydroxycarboxylic acid, for example, such as lactide or glycolide, can also be used as the raw material. Furthermore, dicarboxylic acids or glycols can also be used.

The polylactic acid-based resin can be prepared by a method of directly dehydration condensing the above-described raw material or a method of ring-opening polymerizing the above-described cyclic ester intermediate. For example, when it is prepared by the direct dehydration condensation, a polymer having a high molecular weight can be prepared by polymerization by a method of serving the lactic acids or the lactic acids and the hydroxycarboxylic acids to azeotropic dehydration condensation preferably under the presence of an organic solvent, in particular, a phenylether-based solvent, preferably, by removing water from the solvent distillated by the azeotrope and returning the solvent controlled at a substantially dehydrated condition to the reaction system.

Further, it is also known that a polymer having a high molecular weight can be prepared by ring-opening polymerizing a cyclic ester intermediate such as lactide under a pressure-reduced condition, using a catalyst such as octyl tin. At that time, a polymer small in amount of lactide can be obtained by employing a method of adjusting the condition of removing the moisture component and the low-molecular compounds in the organic solvent at the time of heat reflux, a method of suppressing a depolymerization by deactivating the catalyst after the polymerization, a method of heat treating the prepared polymer or the like.

When used as a drug delivery system by providing a layer containing a chemical at an interlaminar part of the polymer laminate or by containing in the layer itself, to achieve a desired time for sustained release of the chemical, the degradation time or the chemical transmittance rate of the biodegradable resin layer can be adjusted by controlling the degree of crystallinity and the degree of polymerization of the polylactic acid-based resin.

Polyvinyl Alcohol

Polyvinyl alcohol is a saponificate of polyvinyl acetate, and the degree of saponification thereof is preferably 85 to 98.5 mol %, and more preferably 85 to 90 mol %. When the degree of saponification of polyvinyl alcohol is more than 98.5 mol %, the solubility of a water soluble resin layer being obtained into water may be reduced.

As a polyvinyl alcohol copolymer, the units of vinyl alcohol thereof are preferably 80 to 98 mol %, and more preferably 85 to 98 mol %. The degree of saponification means a rate (mol %) of the mol number of the vinyl alcohol units relative to the total mol number of the structural units capable of being converted into vinyl alcohol units by saponification (typically, vinyl ester units) and the vinyl alcohol units contained in the polyvinyl alcohol or the copolymer thereof. The degree of saponification can be determined based on JIS K6726:1994.

The average degree of polymerization of polyvinyl alcohol is preferably 100 to 5,000, more preferably 200 to 2,500, and further preferably 400 to 1,800. The average degree of polymerization means a number average degree of polymerization. If the average degree of polymerization is in this range, since a uniform coating film is easily formed, the mechanical strength as the coating film is high and it is excellent in re-solubility in an aqueous solution, such a condition is preferred. The average degree of polymerization means an average degree of polymerization determined based on JIS K6726:1994.

Two kinds or more of water soluble polymers having different average degrees of polymerization may be mixed and used. By this, in addition to high mechanical strength and re-solubility in an aqueous solution as a coating film, a good performance coating film in close adherence with the polylactic acid-based resin can be obtained. It is preferred to mix and use two kinds or more of water soluble polymers of a water soluble polymer having a low average degree of polymerization of 100 to 800 and a water soluble polymer having a high average degree of polymerization of 1,000 to 2,500. The water soluble polymer having a low degree of polymerization preferably has an average degree of polymerization of 300 to 700. The water soluble polymer having a high degree of polymerization preferably has an average degree of polymerization of 1,300 to 1,700.

Various kinds of additives may be contained at 30 mass % or less relative to 100 mass % of the whole of the respective layers as long as the content is within a range which does not damage the desired effects. The lower limit is not particularly restricted, and there is no problem even if it is 0 mass %. As the various kinds of additives, an antioxidant, a thermal stabilizer, a lubricant, a nucleating agent, an ultraviolet absorber, a colorant or the like can be used. Further, inorganic or organic particles may be contained at 20 mass % or less as long as the content is within a range which does not damage the desired effects. The lower limit is not particularly restricted, and there is no problem even if it is 0 mass %. For example, calcium carbonate, titanium oxide, silicon oxide, calcium fluoride, lithium fluoride, alumina, barium sulfate, zirconia, calcium phosphate, cross-linked polystyrene-based particles or metal nanoparticles or the like can be used.

Alginate

It is also preferred to use an alginate as a polysaccharide. Although the alginate is not particularly restricted, to dissolve the alginate into water, usually it is preferred to use it at a condition of a salt with a monovalent metal ion such as sodium, potassium or the like. The weight average molecular weight thereof is preferably usually at least 50,000 or more, and more preferably 80,000 to 400,000. If the weight average molecular weight of the alginate is in this range, since a uniform coating film is easily formed, the mechanical strength as the coating film is high and it is excellent in re-solubility in an aqueous solution, such a condition is preferred.

Alginate forms a salt with a divalent or more metal ion, and becomes a hydrogel insoluble into water. As the divalent metal ion, an alkaline-earth metal such as beryllium, magnesium, calcium, strontium, barium and radium can be exemplified, and as the trivalent or more metal ion, aluminum, yttrium, zirconium, iron or other transition metal ions can be exemplified. The above-described polyvalent metal ions can be added to water at a form of a salt such as a hydroxide, a chloride or a nitrate, and may be used as an ion produced by dissociation. By gelling the alginate region in the laminate with the above-described metal ion, in addition that the whole of the laminate comprising the polylactic acid-based resin and the alginate can be obtained as a single sheet, it is advantageous to improve the handling ability when the outermost layers are joined to each other.

The gelled alginate region in the polymer laminate can be dissolved with a chelating agent. As typical chelating agents, acids such as carboxylic acid base, phosphonic acid base or hydroxy acid base and the salts thereof are general, for example, general organic carboxylic acids such as succinic acid, gluconic acid, oxalic acid, citric acid or tartaric acid and salts thereof, amino-carboxylic acids such as ethylene diamine tetraacetic acid (EDTA), nitrile triacetic acid (NTA), diethylene triamine pentaacetic acid (DTPA), hydroxy ethylethylene diamine triacetic acid (HEDTA), triethylene tetramine hexaacetic acetate (TTHA), 1,3-propane diamine tetraacetic acid 1,3-PDTA), 1,3-diamino-2-hydroxypropanoic tetraacetic acid (DTPA-OH), or hydroxy-ethyl imino diacetic acid (HEIDA), and salts thereof, phosphonic acids such as hydroxy ethylidene diphosphoric acid, nitrilotris (methylene phosphoric acid), phosphono butane tricarboxylic acid, ethylene diamine tetra (methylene phosphoric acid), adenosine triphosphoric acid (ATP), etidronic acid, metaphosphoric acid (polyphosphoric acid), or phytic acid, and salts thereof, and hydroxy acids such as malic acid or citric acid and salts thereof, can be exemplified.

Figure 5:
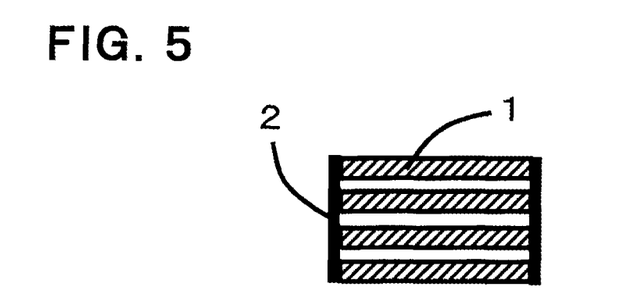
FIG. 5 is a sectional view of a polymer laminate according to a further example.
Figure 6:
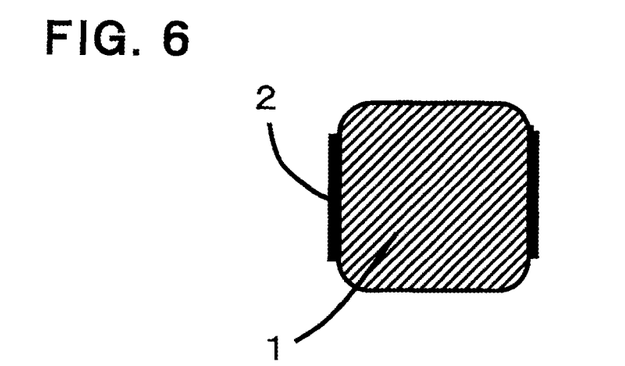
FIG. 6 is a plan view of the polymer laminate shown in FIG. 5 as seen from above.
Figure 7:
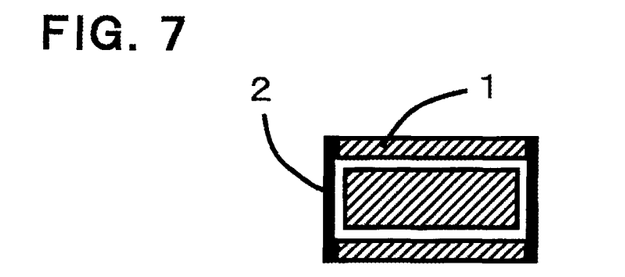
FIG. 7 is a sectional view of a polymer laminate according to a still further example.
Figure 8:
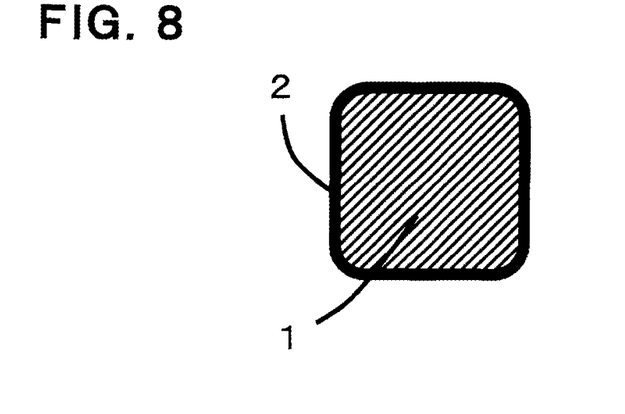
FIG. 8 is a plan view of the polymer laminate shown in FIG. 7 as seen from above.

When the joining formations of outermost layers as shown in FIGS. 1 to 6 are formed, after the alginate is dissolved by a chelating agent, the alginate may be removed by dipping the laminate in an aqueous solution, and in a joining formation shown in FIGS. 7 and 8, it may be enclosed inside the laminate by being liquefied.

Additive

Various kinds of additives may be contained at 30 mass % or less relative to 100 mass % of the whole of the respective layers as long as they do not damage the desired effects. As the various kinds of additives, an antioxidant, a weathering stabilizer, a thermal stabilizer, a lubricant, a nucleating agent, an ultraviolet absorber, a colorant and the like can be used. The lower limit of the content of the additives is not particularly restricted, and there is no problem even if it is 0 mass % relative to 100 mass % of the whole of the respective layers.

Particles

Inorganic or organic particles may be contained at 20 mass % or less relative to 100 mass % of the whole of the respective layers as long as they do not damage the desired effects. For example, latex beads, calcium carbonate, titanium oxide, silicon oxide, calcium fluoride, lithium fluoride, alumina, barium sulfate, zirconia, calcium phosphate, cross-linked polystyrene-based particles or metal nanoparticles, particles contained with chemicals (liposome or micelle or the like) and the like can be used. The lower limit of the content of the inorganic or organic particles is not particularly restricted, and there is no problem even if it is 0 mass % relative to 100 mass % of the whole of the respective layers. Further, the particles either may be contained in the layers themselves or may be contained at interlaminar parts. Further, the diameter of the particles is preferably 5 nm to 5,000 nm, and more preferably 50 nm to 1,000 nm. If the diameter of the particles is smaller than 5 nm, the dispersibility thereof in a coating material may be poor, and if greater than 5,000 nm, the close adherence to the polymer laminate may be poor. Furthermore, the particles may be particles whose surfaces are modified with a chemical such as a transferrin receptor or another material combining with a tumor-specific antigen (transferrin or various antibodies).

Chemicals

For example, an anticancer drug, an antibiotic or the like for the purpose of treatment, diagnosis, precaution, pain relief or the like for a human body or an animal can be exemplified.

Method of Using a Polymer Laminate

The polymer laminate may be used as it is, and may be used as a condition of being laminated with another material. Other material is not particularly restricted as long as it is a generally used material, a metal such as silver or aluminum or an oxide thereof, a paper, a biomembrane, a resin film, a nonwoven fabric or the like can be exemplified.

The biomembrane indicates a membrane that surrounds various cells and small cell organs, further, the cells include various internal organs, organs, cells of organization, blood cells, generative cells or the like and, furthermore, the small cell organs indicate tangible components of cytoplasm having a certain level of function, and include a golgi body, a mitochondria, a centriole, a ribosome, an endoplasmic reticulum, a lysosome, a nuclear membrane or the like.

As the resin film, a non-stretched film, a biaxially stretched film, a coextruded film, a coated film, a deposited film, a melt-extruded resin or the like can be used, and as the raw materials thereof, can be used a polyolefin such as polyethylene and polypropylene, a polyester such as polyethylene terephthalate, polybutylene terephthalate and polyethylene-2,6-naphthalate, a polyamide such as nylon 6 and nylon 12, polyvinyl chloride, polyvinylidene chloride, polyvinyl acetate or a saponificate thereof, ethylene-vinyl acetate copolymer or a saponificate thereof, polystyrene, an aromatic polyamide, an ionomer resin, polycarbonate, polysulfone, polyphenylene oxide, polyphenylene sulfide, polyimide, polyamideimide, cellulose, cellulose acetate, polyacrylonitrile, and copolymers thereof.

As the nonwoven fabric, a fibrous structure obtained by forming a fleece using a dry method, a wet method, a spun bond method or the like, and connecting between fibers using a chemical bond method, a thermal bond method, a needle punch method, a water complex method or the like can be used.

Further, the lamination structure with another material is not particularly restricted, and a printed layer, an adhesive layer or an anchor layer may be present between the polymer laminate and the other material.

Production Method

Next, although a typical method of producing the polymer laminate will be described, it is not limited to the following method.

Method of Forming a Coating Film

Although the method of preparing a polymer laminate is not particularly restricted, there is a method of, after providing a polymer laminate on a base plate composed of a silicon, a glass, a metal, a resin film or the like by repeating coating and drying of a solution dispersed with components containing a biodegradable resin in various solvents on the base plate, delaminating it from the base plate to obtain a polymer laminate as a single substance. Although the delamination method is not particularly restricted, there are a method of obtaining a polymer laminate by mechanically delaminating it, a method of obtaining a polymer laminate by dissolving a water soluble resin layer (a sacrificial layer) provided at an interface between the base plate and the polymer laminate by dipping it in an aqueous solution, thereby removing the water soluble resin layer or the like. As the aqueous solution, various aqueous solutions such as calcium chloride aqueous solution, ethylene diamine tetraacetate aqueous solution, sodium chloride aqueous solution, glucose solution and buffer solution can be used and, in particular, water is preferably used. Further, as the other method, there is a method or the like for laminating a biodegradable resin in a die and extruding the laminate from the die in a film form.

Further, although the coating method onto the base plate used to obtain a polymer laminate is not particularly restricted, the solution dispersed with components containing a biodegradable resin in various solvents is preferably served to spin coating, gravure coating, reverse coating, spray coating, kiss coating, comma coating, die coating, knife coating, air knife coating or metering bar coating. When the biodegradable resin is a resin having a dissolvability into an organic solvent such as a polylactic acid-based resin, it is performed preferably at a temperature for drying of 50° C. to 110° C. and a time for drying of 1 second to 120 seconds. When the biodegradable resin is a water soluble resin such as an alginate or a polyvinyl alcohol, in an off-line coating, it is performed preferably at a temperature for drying of 50° C. to 180° C. and a time for drying of 1 second to 120 seconds.

To the base plate, a treatment of stabilizing the shape of a coating film before coating may be performed, for example, such as a corona discharge treatment in air, in nitrogen gas, in a nitrogen/carbon dioxide mixture gas, or under another atmosphere condition, a plasma treatment under a pressure-reduced condition, a flame treatment, an ultraviolet treatment, or an anchoring treatment using an anchoring treatment agent such as an urethane resin, an epoxy resin or a polyethylene imine. Further, to adjust the releasing property from the base plate, a mold releasing treatment using a silicone or a fluorine containing compound may be performed.

Coating Material when the Biodegradable Resin is a Resin Having a Dissolvability into an Organic Solvent The organic solvent used to prepare the coating material is not particularly restricted as long as it can dissolve the biodegradable resin uniformly.

For example, in a coating material containing a polylactic acid-based resin, it is preferred to use a mixture solution containing at least one selected from the group consisting of butyl alcohol, chloroform, cyclohexane, acetonitrile, dichloromethane, dichloroethane, ethyl acetate, ethyl ether, dipropyl ether, toluene and hexafluoroisopropanol.

Further, although the concentration of solid component of the coating material containing a biodegradable resin is not particularly restricted, it is preferably 0.1 mass % or more and 20 mass % or less from the viewpoint of the productivity such as the viscosity, the drying efficiency or the coatability of the coating material.

Furthermore, to give an application ability, another organic compound as a third component may be contained in the solution as long as its content is within a range at which the stability of the coating material containing a biodegradable resin can be maintained.

Coating Material when the Biodegradable Resin is a Water Soluble Resin

Although the water solvent used to prepare the coating material is not particularly restricted as long as it can dissolve the biodegradable resin uniformly, a purified water or a mixture solution of water/lower alcohol is preferably used.

The concentration of solid component of the coating material containing a biodegradable resin is preferably 1.0 mass % or more and 20 mass % or less from the viewpoint of the productivity such as the viscosity, the drying efficiency or the coatability of the coating material. If a high-concentration coating material more than 20 mass % is used, the viscosity of the solution becomes too high, and it becomes difficult to control the thickness of the biodegradable resin. When a low-concentration coating material less than 1.0 mass % is used, a method of adding a low-boiling point solvent high in volatility and having a compatibility with water to the solvent of the coating material, a method of performing the drying of the coating film at a temperature of the boiling point of water or higher or the like can be used.

Further, to provide an application ability, another water soluble organic compound as a third component may be contained in the solution as long as its content is within a range at which the stability of the coating material containing a biodegradable resin can be maintained. As the above-described water soluble organic compound, for example, alcohols such as methanol, ethanol, n-propanol and isopropanol, glycols such as ethylene glycol and propylene glycol, glycol derivatives such as methyl cellosolve, ethyl cellosolve and n-butyl cellosolve, polyhydric alcohols such as glycerin and wax groups, ethers such as dioxane, esters such as ethyl acetate, ketones such as methyl ethyl ketone or the like can be raised.

Preparation Method of Coating Material

Although the preparation method of the coating material is not particularly restricted, when various additives such as chemicals, cross-linking agents or particles are added within a range which does not damage the desired effects, it is preferred that the resin and the additives are uniformly dispersed in the coating material. As needed, a method of enhancing the solubility of the resin by raising the temperature of the solvent, or a method of employing a mechanically forcible dispersion treatment using a device such as homo mixer, a jet agitor, a ball mill, a bead mill, a kneader, a sand mill or a three-roll mechanism can be employed.

Method of Inserting Particles into an Interlaminar Part of the Laminate

Although the method of inserting particles into an interlaminar part of the laminate is not particularly restricted, a method of dipping the laminate having a water soluble resin layer prepared by the above-described method in a purified water, dissolving the water soluble resin layer, after making a laminate composed of only resin layers having a dissolvability to an organic solvent, dipping it in an aqueous solution dispersed with particles, and inserting the particles into an interlaminar part by capillary phenomenon, and the like, can be exemplified.

EXAMPLES

Hereinafter, our laminates and methods will be further explained based on Examples.

Methods of Evaluating Properties

The methods of evaluating properties are as follows.

(1) Thickness of Each Layer:

A section of a polymer laminate was cut out by a microtome (supplied by Nihon Microtome Laboratory, Inc., RMS), and the thickness of each layer was determined by observing the section with a scanning electron microscope.

(2) Total Thickness:

The total thickness was determined using fine shape measuring instruments (step meter/film thickness meter) (supplied by Kosaka Laboratory Ltd., ET200). At the same time, the section was observed using a scanning electron microscope (supplied by Hitachi High-Technologies Corporation, FE-SEM S-4800).

(3) Close Adherence with Silicon Base Plate:

A polymer laminate was suspended in water and adsorbed to a silicon base plate. The silicon base plate adhered with the polymer laminate was taken out from the water, and dried (temperature: 50° C., 10 to 15 hours). A scratch test was performed relatively to a surface of the polymer laminate using an ultrathin film scratch tester (supplied by Rhesca Corporation, Model CSR-200), at the following condition.

Scratch speed: 10 μm/sec.
Excitation level: 100 μm
Applied load speed: 0.17 mN/sec.
Radius of curvature of diamond indenter: 25 μm The value of a load for delamination obtained was amended using the film thickness of each sheet and Equation 1, and was evaluated by the following ranks.

Strength of close adherence ($\times 10^5$ N/m)=value of load for delamination (N)/film thickness (m)　　Equation 1:

Strength of $0.80 \times 10^5$ N/m or more was determined to be Rank S, strength of $0.70 \times 10^5$ N/m or more and less than $0.80 \times 10^5$ N/m was determined to be Rank A, strength of $0.60 \times 10^5$ N/m or more and less than $0.70 \times 10^5$ N/m was determined to be Rank B, and strength less than $0.60 \times 10^5$ N/m was determined to be Rank C.

Figure 9:
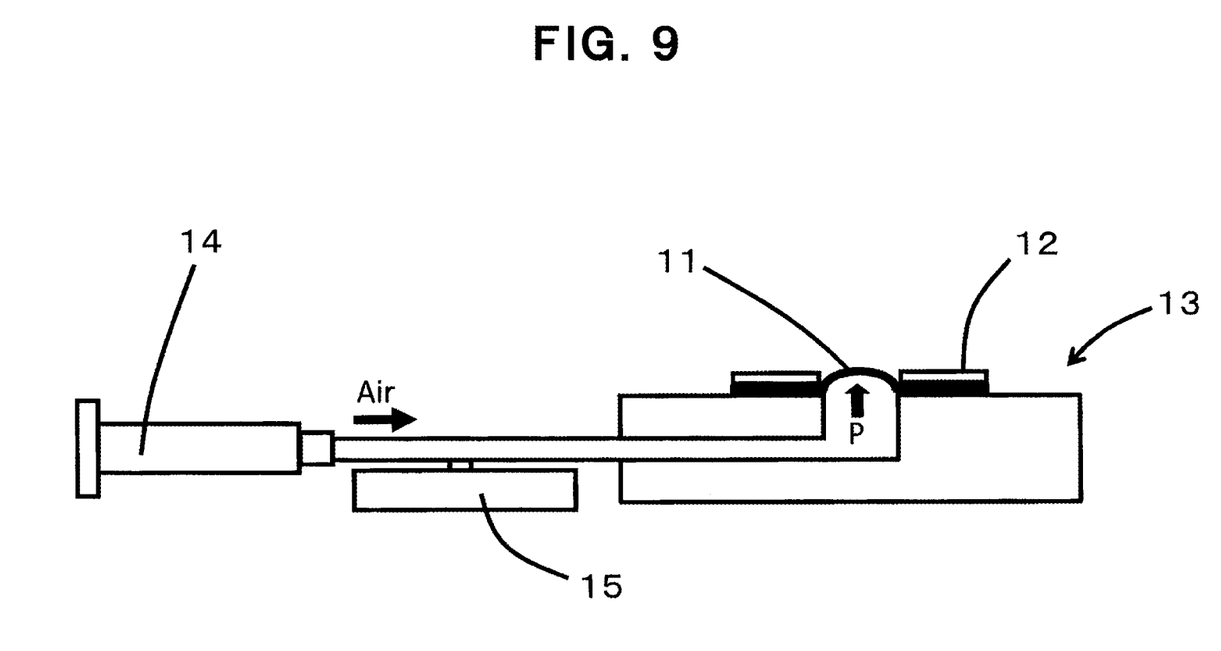
FIG. 9 is an explanation diagram showing a method of determining rupture strength.

(4) Rupture Strength:

As shown in FIG. 9, a sample 11 for determination of a polymer laminate was adsorbed to a washer 12 (outer diameter: 40 mm, hole diameter: 2.5 mm), and they were fixed to a bulge testing machine 13. Using a syringe pump 14 (supplied by AS ONE Corporation, SPS-1), air was sent at 3 mL/min., an air pressure when the polymer laminate was ruptured was determined by a gauge pressure gauge 15 (supplied by OKANO WORKS, LTD., GPG104C11), and the rupture strength was evaluated by the following ranks.

Strength of 22.0 kPa or more was determined to be Rank S, strength of 2.4 kPa or more and less than 22.0 kPa was determined to be Rank A, strength of 1.7 kPa or more and less than 2.4 kPa was determined to be Rank B, and strength less than 1.7 kPa was determined to be Rank C.

(5) Photograph of Section:

It was observed using a confocal laser scanning microscope (supplied by Olympus Corporation, FV-1000D).

Used Base Plate

A P-type silicon wafer supplied by KST World Corp. (diameter: 100±0.5 mm, thickness: 525±25 µm, oxide film: 200 nm, crystal plane: (100)) was used at a cut size of 40 mm×40 mm.

Used Polylactic Acid (PLA)-Based Resin

PLLA-1

Poly-L-lactic acid-based resin having a melting point of 173 to 178° C. and a weight average molecular weight of 80,000 to 100,000 (supplied by Polysciences, Inc.)

Used Water Soluble Resin

PVA-1

Polyvinyl alcohol (PVA) of 25 mass % aqueous solution having a degree of saponification of 86.5 to 89% and a degree of polymerization of 500 (weight average molecular weight: 22,000) (supplied by KANTO CHEMICAL CO., INC.)

Alginate-1

Sodium alginate having a degree of polymerization of 450 (weight average molecular weight: 100,000) (supplied by KANTO CHEMICAL CO., INC., Cica rank 1)

Used Protein

A bovine serum albumin supplied by Sigma-Aldrich Co. LLC. (BSA) (purity: 98%)

It was labelled with the following red marker.

Used Marker

Green marker: "3,3-octadecyl oxacarbocyanine perchlorate" supplied by Invitrogen Corporation (DiOC18)

Red marker: "Tetramethyl rhodamine isothiocyanate" supplied by Sigma-Aldrich Co. LLC. (TRITC)

Used Particles

Latex beads 1: latex particles supplied by Polysciences, Inc. (diameter: 200 nm)

Latex beads 2: latex particles supplied by Polysciences, Inc. (diameter: 1,000 nm)

Used Coating Material

PLLA Solution-1

PLLA-1 was dissolved in dichloromethane using a stirrer to prepare a solution with a solid component concentration of 10 mg/mL. Further, since the film thickness after drying of a PLLA resin layer was in proportion to the solid component concentration of PLLA when spin coated, based on that, the solid component concentration of PLLA was appropriately adjusted.

PLLA Solution-2

0.18 part of the green marker was added relative to 100 parts of PLLA solution-1, and it was stirred by a stirrer to prepare a mixed solution.

PVA• Alginate Mixed Solution-1

Using a stirrer, PVA-1 and alginate-1 were dissolved into water to prepare a mixed solution with a solid component concentration of 20.5 mg/mL (solid component concentration of PVA-1: 2.5 mg/mL, solid component concentration of alginate-1: 18 mg/mL).

PVA• Alginate Mixed Solution-2

0.13 part of albumin labelled with the red marker was added relative to 100 parts of PVA• alginate mixed solution-1, and it was stirred by a stirrer to prepare a mixed solution.

Example 1

Process 1: Coating of Sacrificial Layer

PVA• alginate mixed solution-1 was spin coated onto a base plate, and it was dried (temperature: 50° C., time: 90 seconds) to obtain a water soluble resin layer (a sacrificial layer) with a film thickness after drying of 230 nm.

Process 2: Coating of PLLA Resin

Next, PLLA solution-1 was spin coated onto the water soluble resin layer (sacrificial layer), and it was dried (temperature: 50° C., time: 90 seconds) to obtain a PLLA resin layer with a film thickness after drying of 60 nm.

Process 3: Coating of PVA• Alginate Mixed Layer

Next, PVA• alginate mixed solution-1 was spin coated onto the PLLA resin layer, and it was dried (temperature: 50° C., time: 90 seconds) to obtain a water soluble resin layer with a film thickness after drying of 230 nm.

Process 4: Coating of PLLA Resin

Next, PLLA solution-1 was spin coated onto the water soluble resin layer (sacrificial layer), and it was dried (temperature: 50° C., time: 90 seconds) to obtain a PLLA resin layer with a film thickness after drying of 60 nm.

Process 5: Gelling of PVA• Alginate Mixed Layer

Next, the laminate prepared in the above-described process 1 to process 4, which was in a condition adhered to the base plate, was dipped in a calcium chloride aqueous solution (solid component concentration: 20 mg/mL) for 30 to 60 minutes (25° C.).

Process 6: Detachment from the Base Plate

Next, the laminate in a condition adhered to the base plate was taken out from the calcium chloride aqueous solution, and after cleaned by being replaced with 50 mL of purified water five times (25° C.), a polymer laminate was detached from the base plate. The polymer laminate was taken out from the purified water, and dried on a nonwoven fabric (50° C., one hour or more).

Process 7: Heat Seal

Figure 1:
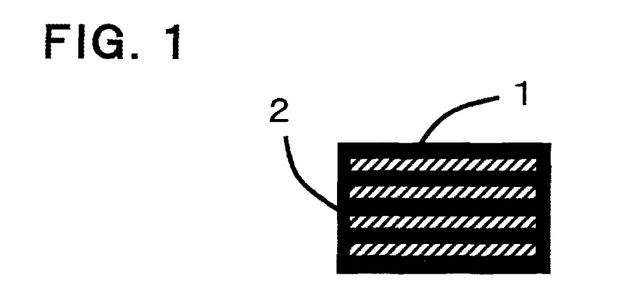
FIG. 1 is a sectional view of a polymer laminate according to an example.

Next, two edges of the polymer laminate were heat cut (187° C., one second) using a Poly sealer (supplied by FUJIIMPULSE CO., LTD., PC-200) so that the joining condition of the outermost layers became the state shown in FIG. 1.

Process 8: Removal of Resin at an Interlaminar Part

Next, the polymer laminate was dipped in an ethylenediamine tetraacetate aqueous solution (0.5 M), and was shaken for 24 hours (37° C.) to dissolve and remove the PVA• alginate mixed layer present between PLLA resin layers. The polymer laminate was taken out from the ethylenediamine tetraacetate aqueous solution, and after cleaned by being replaced with 50 mL of purified water five times, it was dried on a nonwoven fabric (50° C., one hour).

Process 9: Heat Seal

Figure 2:
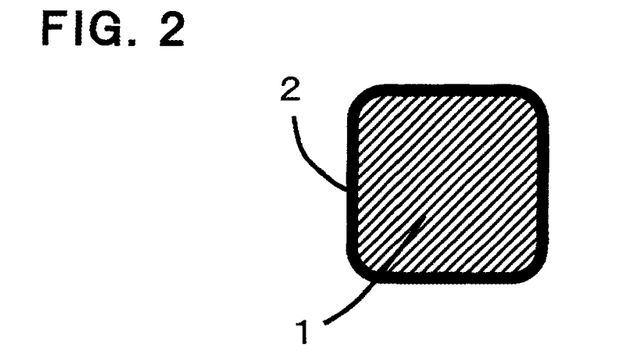
FIG. 2 is a plan view of the polymer laminate shown in FIG. 1 as seen from above.

Next, the remaining two edges of the polymer laminate were heat cut using the Poly sealer (supplied by FUJIIMPULSE CO., LTD., PC-200) to become the state shown in FIG. 2, to obtain a polymer laminate comprising PLLA-1 (approximately, 40 mm×40 mm). The joining state was shown as Formation A (FIGS. 1 and 2). The properties of the obtained polymer laminate are shown in Table 1.

Example 2

A polymer laminate was prepared in a manner similar to that in Example 1 other than a condition controlling the thickness of after drying of PLLA resin layer at 10 nm. The properties of the obtained polymer laminate are shown in Table 1.

Example 3

Figure 3:
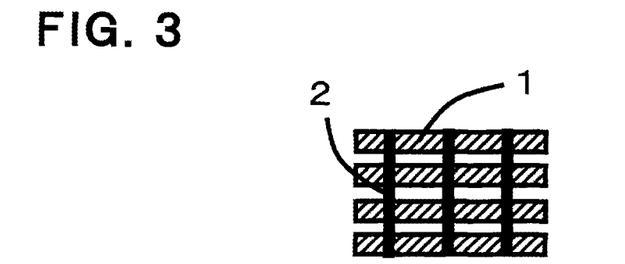
FIG. 3 is a sectional view of a polymer laminate according to another example.
Figure 4:
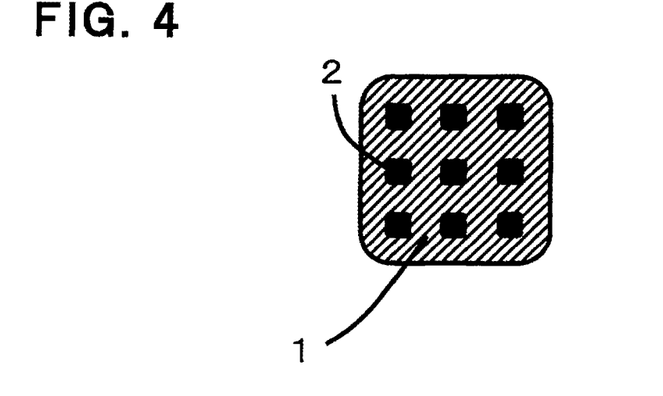
FIG. 4 is a plan view of the polymer laminate shown in FIG. 3 as seen from above.

A polymer laminate was prepared in a manner similar to that in Example 1 other than conditions controlling the thickness of after drying of PLLA resin layer at 180 nm and forming the joining state at Formation B (FIGS. 3 and 4). The properties of the obtained polymer laminate are shown in Table 1.

Columnar projections each having a diameter of 2 mm and a height of 2 mm were provided to upper and lower hot plates used for heat seal so that the distance between the centers of the columns becomes 10 mm, the positions of the upper and lower hot plates were adjusted so that the projections are confronted to each other, and by controlling the temperatures of the both hot plates at 190° C. and press contacting them to a polymer laminate, 16 joining portions were provided uniformly to the polymer laminate (approximately, 40 mm×40 mm).

Example 4

A polymer laminate was prepared in a manner similar to that in Example 1 other than conditions controlling the thickness of after drying of PLLA resin layer at 10 nm, repeating the processes 3 and 4 described in Example 1 to control the number of lamination at 100 layers and forming the joining state at Formation B (FIGS. 3 and 4). The properties of the obtained polymer laminate are shown in Table 1.

Example 5

A polymer laminate was prepared in a manner similar to that in Example 4 other than conditions controlling the thickness of after drying of PLLA resin layer at 30 nm and controlling the number of lamination at 21 layers. The properties of the obtained polymer laminate are shown in Table 1.

Example 6

A polymer laminate was prepared in a manner similar to that in Example 1 other than conditions controlling the thicknesses of after drying of two PLLA resin layers at 10 nm and 200 nm and forming the joining state at Formation C (FIGS. 5 and 6). The properties of the obtained polymer laminate are shown in Table 1.

Example 7

A polymer laminate was prepared in a manner similar to that in Example 4 other than conditions forming a three layer structure controlled with the thicknesses of after drying of PLLA resin layers at 10 nm, 100 nm and 30 nm in order and forming the joining state at Formation C (FIGS. 5 and 6). The properties of the obtained polymer laminate are shown in Table 1.

Example 8

A polymer laminate (PLLA resin layer/PVA• alginate mixed layer/PLLA resin layer) was prepared in a manner similar to that in Example 1 other than conditions controlling the thicknesses of after drying of two outermost PLLA resin layers at 60 nm, controlling the thickness of the PVA• alginate mixed layer of process 2 at 380 nm, not carrying out process 7 and the following thereof and forming the joining state at Formation D (FIGS. 7 and 8). The properties of the obtained polymer laminate are shown in Table 1.

Example 9

Figure 10:
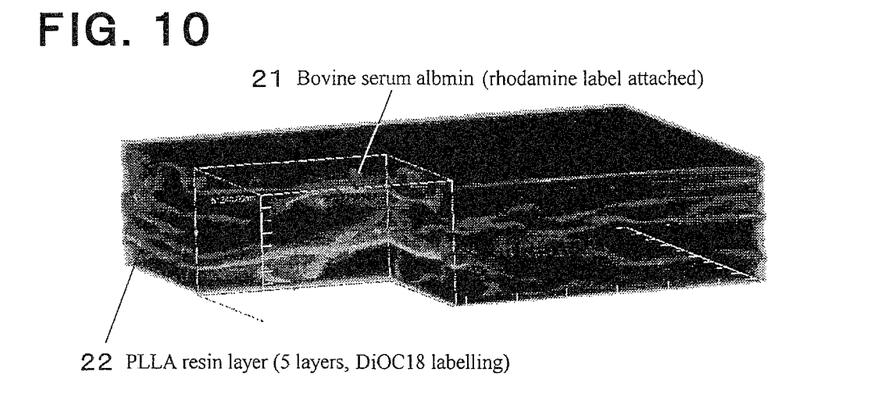
FIG. 10 is a diagram showing a sectional image of a polymer laminate in Example 9 taken by a confocal laser scanning microscope.
Figure 11:
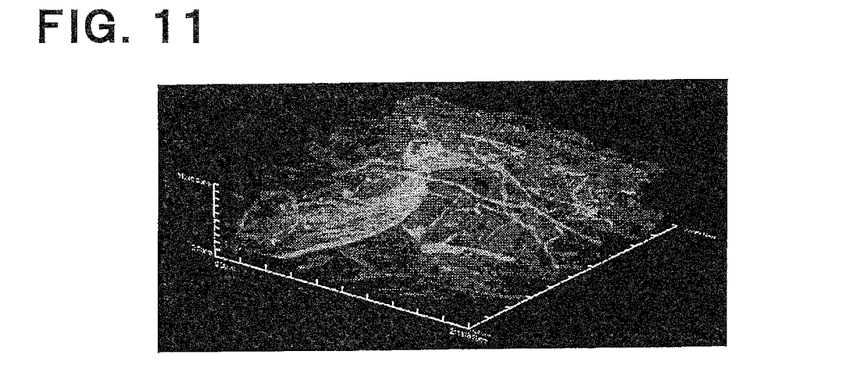
FIG. 11 is a diagram showing a sectional image of the polymer laminate of FIG. 10 as viewed from another angle.

A polymer laminate (PLLA resin layer/PVA• alginate mixed layer/PLLA resin layer/PVA• alginate mixed layer/PLLA resin layer/PVA• alginate mixed layer/PLLA resin layer/PVA• alginate mixed layer/PLLA resin layer) was prepared using process 1 to process 6 of Example 1 other than conditions using PLLA solution-2 and PVA• alginate mixed solution-2 instead of PLLA solution-1 and PVA• alginate mixed solution-1, controlling the thickness of after drying of PVA• alginate mixed layer of process 3 at 170 nm and controlling the number of PLLA resin layers at 5 layers. Further, four edges of the polymer laminate were heat cut (187° C., one second) using a Poly sealer (supplied by FUJIIMPULSE CO., LTD., PC-200) so that the joining condition of the outermost layers became the state shown in FIG. 2, and it was dipped in a phosphate buffer dissolved with trisodium citrate (0.5 M) for 24 hours. Thereafter, the polymer laminate was taken out, and after cleaned by being replaced with 50 mL of purified water five times, it was dried on a nonwoven fabric (50° C., one hour). The properties of the obtained polymer laminate are shown in Table 1, and the section thereof is shown in FIGS. 10 and 11. In FIG. 10, symbol 21 indicates the aforementioned bovine serum albumin (attached with rhodamine label as the aforementioned red marker for labelling), and symbol 22 indicates PLLA resin layers (5 layers, labelled with DiOC18 as the aforementioned green marker for labelling), respectively.

Example 10

Figure 12:
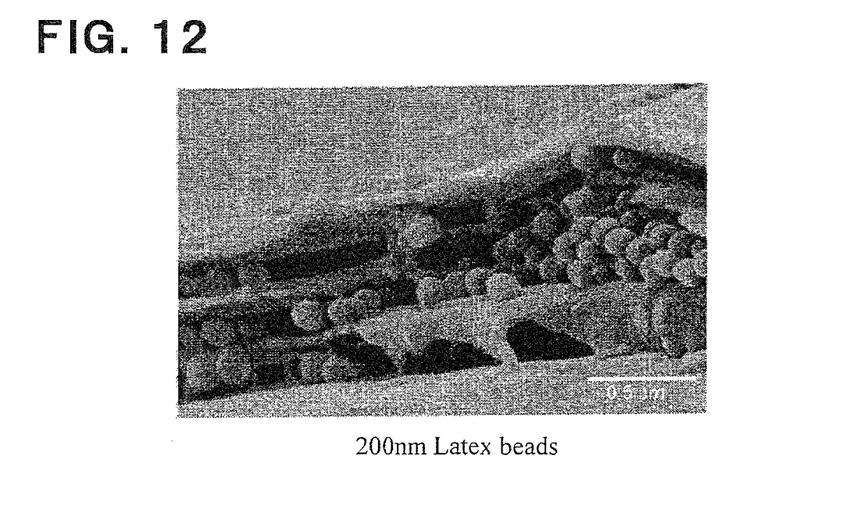
FIG. 12 is a diagram showing a sectional image of a polymer laminate in Example 10 taken by a scanning electron microscope.

A polymer laminate was prepared through process 1 to process 8 described in Example 1. Next, the polymer laminate was dipped in a dispersion dispersed with latex beads-1 at a solid component concentration of 0.25 wt. %, and shaken for 24 hours. Thereafter, the polymer laminate was gently taken out, the remaining two edges of the polymer laminate were heat cut (187° C., one second) using the Poly sealer (supplied by FUJIIMPULSE CO., LTD., PC-200) so that the joining condition of the outermost layers became the state shown in FIG. 2, and it was cleaned by being replaced with purified water three times. The properties of the obtained polymer laminate are shown in Table 1, and the section thereof is shown in FIG. 12.

Example 11

Figure 13:
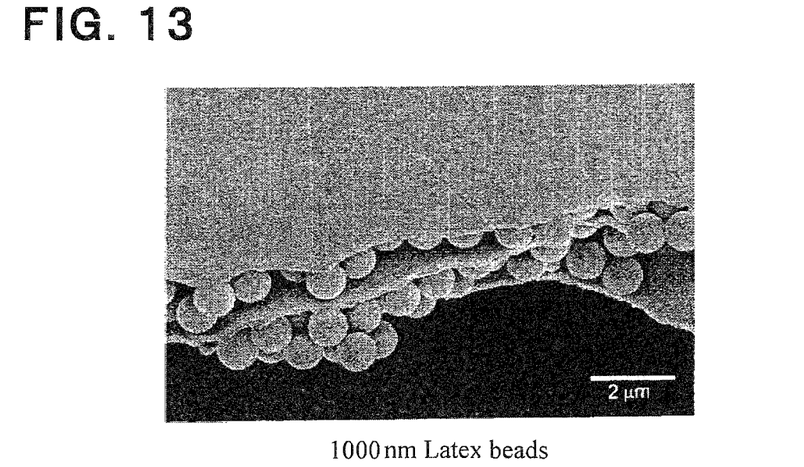
FIG. 13 is a diagram showing a sectional image of a polymer laminate in Example 11 taken by a scanning electron microscope.

A polymer laminate was prepared in a manner similar to that in Example 10 other than a condition using latex beads-2 as the particles. The properties of the obtained polymer laminate are shown in Table 1, and the section thereof is shown in FIG. 13.

Comparative Example 1

A single-layer polymer film was prepared in a manner similar to that in Example 1 other than conditions controlling the thickness of after drying of the PLLA resin layer at 500 nm and not carrying out processes 3 and 4 and process 7 and the following thereof. The properties of the obtained polymer film are shown in Table 2.

Comparative Example 2

A polymer laminate was prepared in a manner similar to that in Example 1 other than a condition controlling the thickness of after drying of the PLLA resin layer at 300 nm. The properties of the obtained polymer laminate are shown in Table 2.

Comparative Example 3

A polymer laminate was prepared in a manner similar to that in Example 4 other than conditions controlling the thickness of after drying of the PLLA resin layer at 60 nm and the number of lamination at 200 layers. The properties of the obtained polymer laminate are shown in Table 2.

Comparative Example 4

When processes 1 to 6 described in Example 1 were carried out and thereafter process 8 was carried out without carrying out process 7, the PLLA resin layer was dispersed in water and a polymer laminate could not be obtained. Namely, as described in Table 2, because the formation could not be kept, it was impossible to determine the properties as a polymer laminate.

TABLE 1

| Item | Detail | Unit | Example 1 | Example 2 | Example 3 | Example 4 | Example 5 | Example 6 |
|---|---|---|---|---|---|---|---|---|
| Outermost layer 1 | Name of resin | — | PLA | PLA | PLA | PLA | PLA | PLA |
| | Thickness | (nm) | 60 | 10 | 180 | 10 | 30 | 10 |
| Intermediate layer | Name of resin | — | — | — | — | PLA | PLA | — |
| | Thickness of each layer | (nm) | 0 | 0 | 0 | 10 | 30 | 0 |
| | Number of layers | — | 0 | 0 | 0 | 98 | 19 | 0 |
| | Name of resin | — | — | — | — | — | — | — |
| | Thickness of each layer | (nm) | — | — | — | — | — | — |
| | Number of layers | — | — | — | — | — | — | — |
| Outermost layer 2 | Name of resin | — | PLA | PLA | PLA | PLA | PLA | PLA |
| | Thickness | (nm) | 60 | 10 | 180 | 10 | 30 | 200 |
| Whole of laminate | Number of layers | — | 2 | 2 | 2 | 100 | 21 | 2 |
| | Total thickness | (nm) | 120 | 20 | 360 | 1,000 | 630 | 210 |
| Joining formation of outermost layers | — | — | Formation A | Formation A | Formation B | Formation B | Formation B | Formation C |
| Close adherence with silicon base plate | Outermost layer 1 | — | S | S | B | B | A | A |
| | Outermost layer 2 | — | S | S | B | B | A | B |
| Rupture strength | — | — | A | B | A | S | S | A |

| Item | Detail | Unit | Example 7 | Example 8 | Example 9 | Example 10 | Example 11 |
|---|---|---|---|---|---|---|---|
| Outermost layer 1 | Name of resin | — | PLA | PLA | PLA | PLA | PLA |
| | Thickness | (nm) | 10 | 60 | 60 | 60 | 60 |

TABLE 1-continued

| | | | | | | | |
|---|---|---|---|---|---|---|---|
| Intermediate layer | Name of resin | — | PLA | Sodium alginate | PLA | PLA | PLA |
| | Thickness of each layer | (nm) | 100 | 380 | 60 | 60 | 60 |
| | Number of layers | — | 1 | 1 | 3 | 1 | 1 |
| | Name of resin | — | — | — | Sodium alginate | — | — |
| | Thickness of each layer | (nm) | — | — | 170 | — | — |
| | Number of layers | — | — | — | 4 | — | — |
| Outermost layer 2 | Name of resin | — | PLA | PLA | PLA | PLA | PLA |
| | Thickness | (nm) | 30 | 60 | 60 | 60 | 60 |
| Whole of laminate | Number of layers | — | 3 | 3 | 9 | 3 | 3 |
| | Total thickness | (nm) | 140 | 500 | 980 | 180 | 180 |
| Joining formation of outermost layers | — | — | Formation C | Formation D | Formation B | Formation B | Formation B |
| Close adherence with silicon base plate | Outermost layer 1 | — | A | A | B | A | A |
| | Outermost layer 2 | — | A | A | A | A | A |
| Rupture strength | — | — | A | A | A | A | A |

TABLE 2

| Item | Detail | Unit | Comparative Example 1 | Comparative Example 2 | Comparative Example 3 | Comparative Example 4 |
|---|---|---|---|---|---|---|
| Outermost layer 1 | Name of resin | — | PLA | PLA | PLA | PLA |
| | Thickness | (nm) | 500 | 300 | 60 | 60 |
| Intermediate layer | Name of resin | — | — | — | PLA | — |
| | Thickness of each layer | (nm) | — | 0 | 60 | 0 |
| | Number of layers | — | — | 0 | 198 | 0 |
| Outermost layer 2 | Name of resin | — | — | PLA | PLA | PLA |
| | Thickness | (nm) | — | 300 | 60 | 60 |
| Whole of laminate | Number of layers | — | 1 | 2 | 200 | 2 |
| | Total thickness | (nm) | 500 | 600 | 12,000 | 120 |
| Joining formation of outermost layers | — | — | — | Formation A | Formation B | Joining: none |
| Close adherence with silicon base plate | Outermost layer 1 | — | C | C | C | — (Formation cannot be kept, determination: impossible) |
| | Outermost layer 2 | — | — | C | C | — (Formation cannot be kept, determination: impossible) |
| Rupture strength | — | — | S | S | S | — (Formation cannot be kept, determination: impossible) |

INDUSTRIAL APPLICABILITY

The polymer laminate can be used also as a drug delivery system in addition to as external skin preparations such as wound dressings, antiadhesive materials and skin-care products. Further, when the outermost layer contains a polylactic acid-based resin, because the sticking surface of the outermost layer is transparent and therefore a scar is not conspicuous, it can be applied not only to surgery operation but also to sticking to a skin, and also to use as a plaster.

The invention claimed is:

1. A polymer laminate, comprising:
   2-100 layers each containing a biodegradable resin and having a thickness of 10 nm-400 nm, a thickness of at least one of outermost layers is 10 nm-180 nm, and
   a joint portion joining said outermost layers at pinpoints, at a part of an end portion of the laminate, at an entire part of the end portion of the laminate, or combinations thereof,
   wherein layers other than the outermost layers may be joined or may not be joined to the outermost layers, and
   said at least one of outermost layers contains a polylactic acid-based resin.

2. The polymer laminate according to claim 1, wherein at least one layer of said layers having a thickness of 10 nm-400 nm contains a compound selected from the group consisting of a polysaccharide, a polyvinyl alcohol and a polyvinyl alcohol copolymer.

3. The polymer laminate according to claim 2, wherein said polysaccharide is an alginate.

4. The polymer laminate according to claim 1, wherein a total thickness of the polymer laminate is 20 nm-1,000 nm.

5. The polymer laminate according to claim 1, wherein a hydrophobic chemical is contained in at least one layer of said layers having a thickness of 10 nm-400 nm.

6. The polymer laminate according to claim 1, wherein a water soluble chemical is contained in at least one layer of said layers having a thickness of 10 nm-400 nm.

7. The polymer laminate according to claim 1, wherein particles having a particle diameter of 5 nm to 5,000 nm are contained in at least one interlaminar part formed between said layers having a thickness of 10 nm-400 nm.

8. The polymer laminate according to claim 2, wherein a total thickness of the polymer laminate is 20 nm-1,000 nm.

9. The polymer laminate according to claim 3, wherein a total thickness of the polymer laminate is 20 nm-1,000 nm.

10. The polymer laminate according to claim 2, wherein a hydrophobic chemical is contained in at least one layer of said layers having a thickness of 10 nm-400 nm.

11. The polymer laminate according to claim 3, wherein a hydrophobic chemical is contained in at least one layer of said layers having a thickness of 10 nm-400 nm.

12. The polymer laminate according to claim 4, wherein a hydrophobic chemical is contained in at least one layer of said layers having a thickness of 10 nm-400 nm.

13. The polymer laminate according to claim 2, wherein a water soluble chemical is contained in at least one layer of said layers having a thickness of 10 nm-400 nm.

14. The polymer laminate according to claim 3, wherein a water soluble chemical is contained in at least one layer of said layers having a thickness of 10 nm-400 nm.

15. The polymer laminate according to claim 4, wherein a water soluble chemical is contained in at least one layer of said layers having a thickness of 10 nm-400 nm.

* * * * *